(12) United States Patent
Miyajima et al.

(10) Patent No.: US 7,780,644 B2
(45) Date of Patent: Aug. 24, 2010

(54) SEALED MEDICAL STORAGE

(75) Inventors: Chiharu Miyajima, Shizuoka (JP); Yasuhiro Muramatsu, Shizuoka (JP)

(73) Assignee: Ajinomoto Co., Inc., Tokyo (JP)

( * ) Notice: Subject to any disclaimer, the term of this patent is extended or adjusted under 35 U.S.C. 154(b) by 156 days.

(21) Appl. No.: 11/544,561

(22) Filed: Oct. 10, 2006

(65) Prior Publication Data
US 2007/0060903 A1 Mar. 15, 2007

Related U.S. Application Data

(63) Continuation of application No. PCT/JP2005/006910, filed on Apr. 8, 2005.

(30) Foreign Application Priority Data

Apr. 8, 2004 (JP) ............................. 2004-114649

(51) Int. Cl.
*A61B 19/00* (2006.01)
(52) U.S. Cl. .................. 604/408; 604/403; 604/416
(58) Field of Classification Search ............... 604/403, 604/408, 410, 414, 415, 416; 383/210.1; 220/62.22
See application file for complete search history.

(56) References Cited

U.S. PATENT DOCUMENTS 4,286,640 A * 9/1981 Knox et al. .................. 604/404
2007/0208320 A1 9/2007 Muramatsu et al.

2008/0033390 A1 2/2008 Kitagawa et al.
2008/0097372 A1 4/2008 Shimizu et al.

FOREIGN PATENT DOCUMENTS

JP 2003-159310 6/2003

(Continued)

OTHER PUBLICATIONS

English language abstract of JP 2004180740 A.*
Enlish language machine translation of JP 2004180740 A.*
U.S. Appl. No. 12/688,427, filed Jan. 15, 2010, Muramatsu, et al.
U.S. Appl. No. 12/512,427, filed Jul. 30, 2009, Muramatsu.
U.S. Appl. No. 12/436,172, filed May 6, 2009, Muramatsu.

*Primary Examiner*—Leslie R Deak
(74) *Attorney, Agent, or Firm*—Oblon, Spivak, McClelland, Maier & Neustadt, L.L.P.

(57) ABSTRACT

A medicine discharge stopper for a medical bag of a type where a multiple of medicines are mixed, aiming to positively exclude a possibility of generation of erroneous operation that administration is done without opening the mixing seal. The medical bag is formed from a soft film and has an inner space, which is divided into compartments 20 and 22. An outlet port 12 is provided so that it is opened to the first compartment 20. The stopper includes split halves, which, when tied, form an inner space 34 of the outlet port 12. The combination is done under a resilient force by cantilever fashioned extending parts 38. When the weak seal portion is opened, an impact-like hydraulic force is generated and the bag is widened, which causes the flaps 30 and 32 to be opened against the resilient force, resulting in a release of the stopper. The flaps 30 and 32 are made separable from the body parts, which allows the stopper to be also utilized for a holder of needle during the execution of infusion process.

16 Claims, 17 Drawing Sheets

FOREIGN PATENT DOCUMENTS

| JP | 2003-305107 | 10/2003 |
| JP | 2004-000661 | 1/2004 |
| JP | 2004180740 A * | 7/2004 |
| JP | 2005-28040 | 2/2005 |
| JP | 2005-028040 | 2/2005 |
| JP | 2005-305136 | 11/2005 |

* cited by examiner

*FIG. 6*
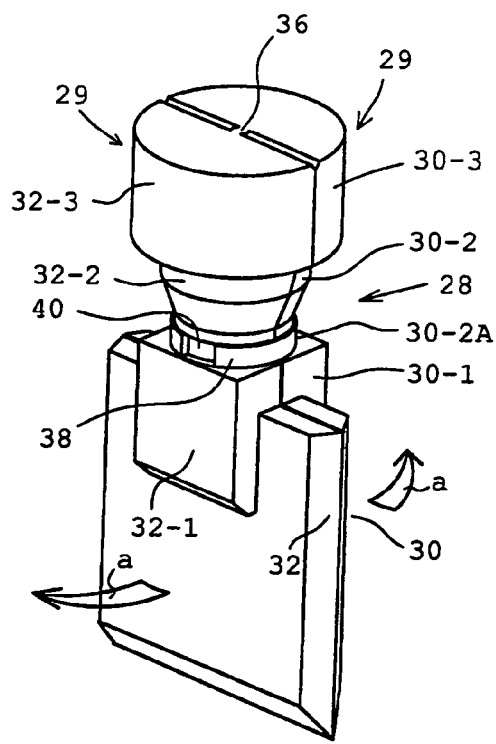
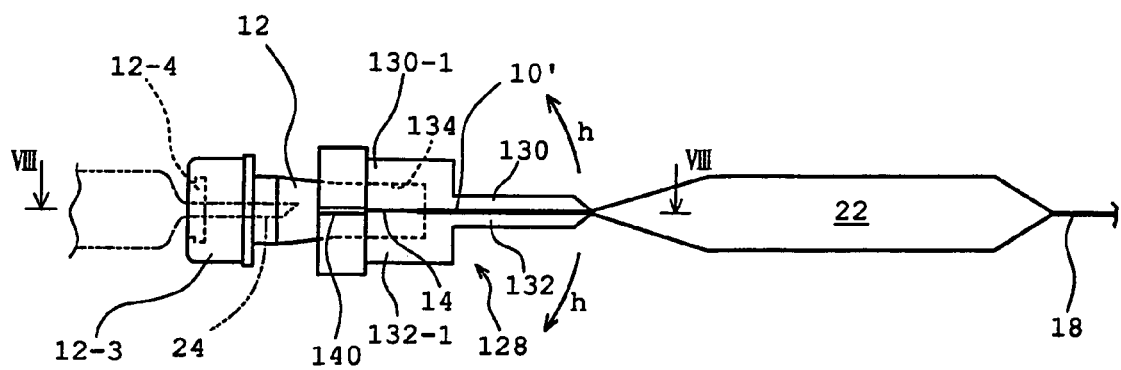
*FIG. 7*

FIG. 12
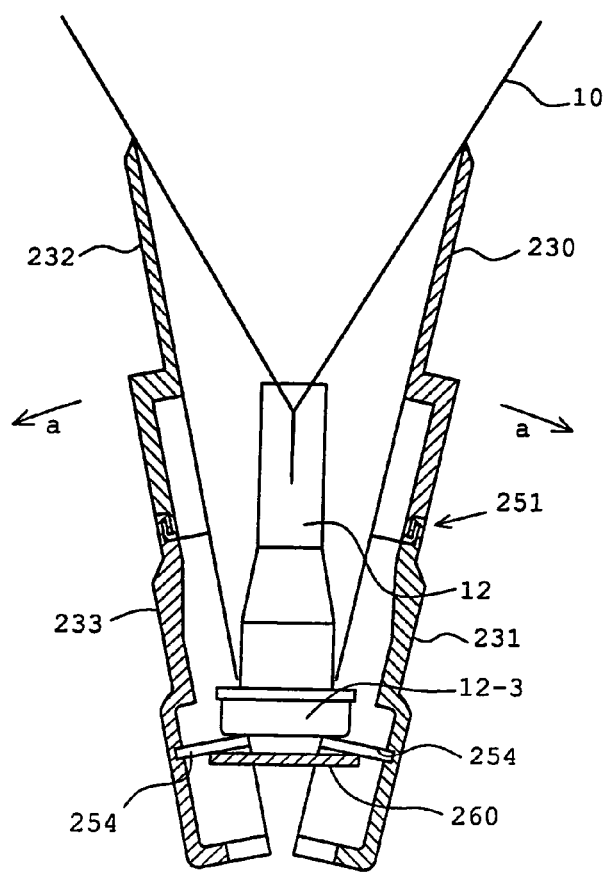
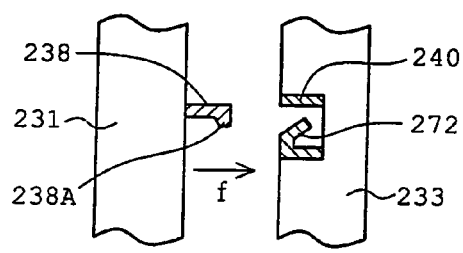
FIG. 13a
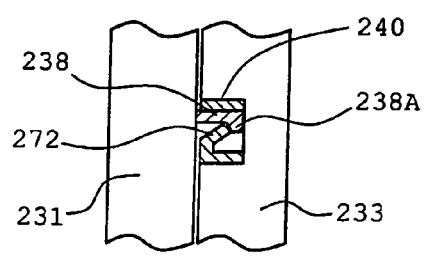
FIG. 13b

SEALED MEDICAL STORAGE

TECHNICAL FIELD

The present invention relates to a sealed medical storage, which has a bag having compartments for storing, in a separate manner, respective medicines, and has a weak sealed portion located between the compartments and opened for causing the medicines to be mixed for use in intravenous dripping or dialyzing.

BACKGROUND TECHNOLOGY

Known is a sealed medical storage of mixing type for use in a intravenous dripping or dialyzing, which is of multi-solution-mixing type. Such a sealed medical storage of mixed type is formed as a bag made of a flexible film and having an inner space, which is divided into compartments by means of a weak sealed portion, which compartments are for separately storing different medical liquids. Arranged at an outer periphery of the bag is an outlet port made as a plastic molded product of a tubular shape. The outlet port has an inner passage, which is, at its first end, opened to one of the compartments and is, at its second end, provided with a plug made of a rubber material. Prior to an administration of the medical liquid to a patient, the medical bag is, at its outside, pressed in a manner that the weak sealed portion is broken. As a result, a single compartment is created in the medical bag, so that the two kind of the medical liquids are mixed with each other. Then, a piercing of the rubber plug by a needle of an infusion set connected to an infusion line is done, which allows an administration of the mixed medical liquid to be possible. In short, in such a sealed storage for medical liquid of mixing type for medical treatment, a step for opening the weak seal portion for mixing both of the liquids is essential prior to the commencement of an administration of the medical liquid. Contrary to this, a piercing of the rubber plug at the liquid outlet without breaking the weak seal portion may cause a wrong operation to be generated that the medical liquid only at the single compartment adjacent the liquid outlet is administered. As a prior art combating this problem, a solution is proposed, wherein, in addition to a first weak seal portion separating the inner cavity of a medical bag into two compartments, a second weak seal portion is provided at a location slightly upstream from the liquid outlet, wherein a pressure for opening the second weak seal is, in comparison with a value of a pressure for opening the first weak seal portion, such that the first weak seal portion is, first, opened and, then, the second weak seal portion is opened, thereby ensuring a discharge of the medical liquids after the completion of the liquid mixing operation. See patent document 1

| Patent document 1: | Unexamined Japanese Patent Publication No. 2004-662 |

DISCLOSURE OF THE INVENTION

Problems to be Solved by the Invention

In the technique disclosed in the Patent Publication No. 1, in addition to a first weak seal separating two compartments, a second weak seal is provided at a location slightly upstream from the liquid outlet, in a manner that the openings of the weak seal portions are occurred under the designated sequence, which is effective for preventing the medical liquids from being administered without being mixed. However, due to the provision of the weak seal portions at two locations, the process for production is complicated, thereby enhancing the production cost. Furthermore, user is forced to execute two-stage opening steps, causing the workability necessarily to be fallen. Furthermore, a manner of pressing of the medical bag does not necessarily ensure the desired sequence that the first weak sealed portion is first opened and, then, the second weak sealed portion is opened. Namely, a situation may occur that the second weak seal portion adjacent the liquid outlet is, first, opened. In this case, a situation is likely arisen that a following infusion process is started without any mixing, resulting in an administration of single liquid only.

The present invention aims to combat the above-mentioned problem and to propose a new structure of medical bag of multi-liquid mixing type, where any administration does not occur so long as the non-opening (no-communication) condition is maintained and aims to obtain a reduced production cost as well as increased operability on user side and, furthermore, aims to more positively eliminate a possibility of an occurrence of erroneous operation that an administration is done under non-mixed condition.

Means for Solving Problem

According to the invention in claim 1, a sealed medical storage is provided, comprising a bag made of flexible material, a weak sealed portion for dividing a space inside the bag into a plurality of compartments, medicines being closely stored in the respective compartments, an outlet port opened to one of said compartments, and a stopper arranged outwardly of the bag for preventing the medicines from being discharged from the outlet port, an arrangement of said stopper being such that said stopper is normally in a condition where a discharge of medicines from the bag is prevented and such that said condition is cancelled by an impact-like hydraulic force as generated in the bag at the instance of the breakage of said weak sealed portion, thereby allowing the medicines to be discharged from said bag.

In an operational effect of the invention in claim 1, the stopper is normally under the condition where a discharge of medicines from the bag is prevented, thereby prohibiting the execution of an infusion process. The weak seal portion is opened by pressing the bag under the entire palm, and, upon the opening of the weak seal portion, the pressing force is rapidly released, which causes an impact-like flow of liquid to be generated in the bag. The impact-like flow of liquid is received by the stopper, which instantly cancels the stopping action of the outflow by the stopper, thereby allowing the infusion process to be commenced. In short, in the present invention, a possibility of an occurrence of an erroneous operation under non-mixed condition prior to the opening of the weak sealed portion is more reliably prevented.

According to the invention in claim 2, a sealed medical storage is provided, comprising a bag made of flexible material, a weak sealed portion for dividing a space inside the bag into a plurality of compartments, different medicines being closely stored in the respective compartments, an outlet port opened to one of said compartments, and a stopper arranged outwardly of the bag for preventing the medicines from being discharged from the outlet port, said stopper comprising a plurality of parts which are relatively movable and a connecting means for connecting said plurality of parts with each other for normally preventing medicines from being discharged from the bag, said connection of said plurality of parts by the connecting means is cancelled by an impact-like fluid force as generated in the bag at the instance of the breakage of said weak sealed portion, thereby allowing the medicines to be discharged from said bag.

In an operational effect of the invention in claim 2, in addition to the operational effect as obtained by the invention of claim 1, the stopper is connect the plurality of movable parts by connecting means, thereby obtaining a more positive prevention of any discharge from the bag under the normal condition, on one hand and, on the other hands, obtaining a more reliable release of the connected movable parts by the impact-like fluid force as generated in the bag at the opening of the weak sealed portion connection, which allows a infusion operation to be smoothly started.

According to the invention in claim 3, a sealed medical storage is provided, comprising a bag made of flexible material, a weak sealed portion for dividing a space inside the bag into a plurality of compartments, medicines being closely stored in the respective compartments, an outlet port opened to one of said compartments, and a stopper arranged outwardly of the bag for preventing the medicines from being discharged from the outlet port, said stopper comprising a pair of parts which are relatively movable and are arranged on respective sides of the bag, each of said parts comprising a contacting portion contacting with opposed surface of the bag, a body portion located on one side of said contacting portion adjacent the outlet port and a connecting means for connecting said relatively movable pair of parts with each other in a manner that a discharge of the medicines from the bag under a normal condition is prevented, the arrangement being such that the connection by said connecting means is cancelled by an impact-like hydraulic force as generated in the bag at the instance of the breakage of said weak sealed portion, thereby allowing the medicines to be discharged from said bag.

In an operational effect of the invention in claim 3, in addition to the operational effect as obtained by the invention of claim 3, the contacting portion is contacted with the faced surface of the medical bag, so that the fluid force generated at the instance of the opening of the weak seal is effectively received and is transmitted to the integrally extended part for releasing the connecting means. Thus, a reliable cancellation of the stoppage of the discharge of the medicine by the stopper is obtained.

According to the invention in claim 4, a sealed medical storage according to claim 1 is provided, wherein said stopper prevents a discharge of a medicine from the bag by preventing access to the outlet port from its outer part.

In an operational effect of the invention in claim 4, the stopper functions to control an access to the outlet port from its outside in a manner that a needle of a infusion set from infusion line is hindered and prohibited even if a piercing is tried, resulting in a positive prevention of infusion process during the non-opened state.

According to the invention in claim 5, a sealed medical storage according to claim 1 is provided, wherein said stopper prevents a discharge of a medicine from the bag by preventing access to the outlet port from its outer part.

In an operational effect of the invention in claim 5, the stopper functions to block a communication of medicines inside the medical bag to the outlet port. Namely, even if a piercing of the needle of an infusion set from infusion line is possible, the medicines cannot be flown into the needle, resulting in a positive prevention of intravenous dripping (operation) during the non-opened state. In this case, the stoppage of communication does not necessarily means that the communication of the medical liquid is completely blocked but includes a situation that a flow amount is limited to a certain degree. In other words, this term includes even the situation that a leakage is occurred so long as the amount of the leakage is small.

According to the invention in claim 6, a sealed medical storage according to claim 2 is provided, wherein said connecting means is of a resilient type connecting means.

In an operational effect of the invention in claim 6, the connection is done under a resilient force, resulting in a positive prevention of the discharge of the medicines from the medical bag during the normal condition, while positive release of the connection is obtained by the impact-like fluid force upon the opening of the weak seal portion irrespective of the resilient force.

According to the invention in claim 7, a sealed medical storage according to claims 2 is provided, wherein said connecting means is an interconnecting means, which is able to be broken by an outside force.

In an operational effect of the invention in claim 7, the connection is done by the interconnecting means able to be broken by an outside force, resulting in a more positive prevention of the discharge of the medicine from the medical bag in the normal state, while a positive disconnection is obtained by a destruction of the interconnecting means by the impact-like fluid force as generated upon the opening of the weak seal portion.

According to the invention in claim 8, a sealed medical storage according to claims 2 is provided, where it further comprises a hinge for integrally connecting said movable parts with each other.

In an operational effect of the invention in claim 8, the provision of the hinge allows the stopper to be made as one pierce product, resulting in a reduction in a number of parts and a reduction in a production cost when the stopper is made as a plastic molded product since a number of necessary die sets is reduced.

According to the invention in claim 9, a sealed medical storage according to claim 6 is provided, wherein said resilient connecting means is integrally formed on said stopper.

In an operational effect of the invention in claim 9, as similar to the invention in claim 8, a reduction in the number of parts is obtained and a reduction in a number of die sets when produced as a plastic mold product is obtained, resulting in a further reduction of production cost.

According to the invention in claim 10, a sealed medical storage according to claim 1 is provided, wherein said stopper includes a chamber outwardly opened at an end remote from said bag and a blocking member, which is detachably mounted to said chamber, said blocking member being provided for preventing any piercing by a infusion set from being occurred and wherein said contacting portion of the stopper is, at its portions contacting with the medical bag, releasable from the remaining body portion, the arrangement being such that, under a condition that said contacting portion is released from the body portion and said blocking member is removed from said chamber, the stopper is mounted to the outlet port pierced by the infusion set in a manner that the infusion set is engaged with the stopper in said chamber, thereby preventing the infusion set from being separated from the bag during the execution of an infusion operation.

In an operational effect of the invention in claim 10, a provision of the blocking member in the chamber of the stopper maintains a basic function of the stopper that any piercing is prevented so long as the stopper is installed to the medical bag. Furthermore, after release of the stopper as a result of the opening of the medical bag, a contacting portion as well as the blocking member are removed from the stopper and then the stopper is, at the chamber, installed to the outlet port, to which an infusion set is pierced, thereby the infusion set to be positively held to the medical bag. Thus, an effective utilization of a used stopper, which is otherwise discarded, is obtained.

According to the invention in claim 11, a sealed medical storage according to claim 10 is provided, wherein said chamber is opened at the end surface of said stopper.

In an operational effect of the invention in claim 11, the chamber has opening at the end surface of the stopper, so that the infusion set is held in its opposite sides, thereby highly enhancing holding ability.

According to the invention in claim 12, a sealed medical storage according to claim 10 is provided, wherein said chamber is opened at the side surface of said stopper.

In an operational effect of the invention in claim 12, the chamber is opened at its side, which allows the infusion set to be installed at its lateral side, thereby enhancing working efficiency.

According to the invention in claim 13, a sealed medical storage is provided, comprising a bag made of flexible material, a weak sealed portion for dividing a space inside the bag into a plurality of compartments, medicines being closely stored in the respective compartments, an outlet port opened to one of said compartments, and a stopper arranged outwardly of the bag for preventing the medicines from being discharged from the outlet port, said stopper forming a chamber opened at its end remote from said bag, said stopper comprising a pair of releasable parts, between which said bag is arranged, a connecting means for causing said pair of parts to be connected in a manner that a discharge of the medicines from the bag under a normal condition is prevented and a blocker member detachably arranged across said chamber in a manner that a piercing by an infusion set is prevented under said connected condition, each of said pair of releasable parts having a portion, which is extended from a body portion of the stopper adjacent said outlet port and which is contacted with a respective opposed surface of said bag, and a linkage means for liking releasably said contacted portion with said body portion.

In an operational effect of the invention in claim 13, an installation of blocking member in the space of the stopper and the releasble linkage of the contacting part by the linkage means makes it possible that a stopper after a completion of its mainly intended use for a blockage of piercing prior to the opening of a medical bag is utilized for preventing the release of a infusion set from a medical bag, as similar to the invention of claim 10.

According to the invention in claim 14, a sealed medical storage according to claim 13 is provided, wherein said opening of said chamber in said stopper is formed between said pair of releasable parts.

An operational effect of the invention in claim 14 is the same as that of claim 11 and thus an increased holding performance is obtained.

According to the invention in claim 15, a sealed medical storage according to claim 13 is obtained, wherein said opening of said chamber is formed laterally in one of said pair of releasable parts.

An operational effect of the invention in claim 15 is the same as that of claim 12 and thus an increased working efficiency is obtained when a holding of an infusion set is done.

According to the invention in claim 16, a method for an infusion is provided, the method is effected by using a medical bag made of flexible material, and having a weak sealed portion dividing a space inside the bag into a plurality of compartments and an outlet port opened to one of said compartments, said method comprising the steps of; providing, prior to an execution of infusion process, a stopper arranged on the bag in a manner that a medicine is prevented from being discharged from said outlet port; of removing said stopper from said outlet port under an impact-like fluid force as generated in the bag at the instance of the breakage of said weak sealed portion; and of piercing said outlet port by an infusion set so that an infusion process is commenced.

An operational effect of the invention in claim 16 is similar to that of the invention of claim 1. Namely, a erroneous operation that an infusion process is commenced prior to the opening of the weak seal portion is more reliably prevented by the stopper, thereby realizing an increased safety of an infusion operation.

According to an embodiment of the invention, a method is provided, wherein said step for providing the stopper comprises the step of providing the stopper having a chamber opened at its end remote from said bag and a blocking member releasably arranged in said chamber in a manner that a piercing by an infusion set is prevented, said stopper having a body part and contacting parts contacting with the medical bag and releasably connected to said body part, and wherein said method further comprises steps; of removing said contacting parts from said body part and removing the blocking member after the removal of said stopper as caused by the breakage of said weak sealed portion; and of mounting, to said outlet port, the stopper after the removal of the contacting parts as well as the blocking member, in a manner that an infusion set is housed in and engaged with the chamber of the stopper, thereby preventing the infusion set from being separated from the outlet port while an infusion process is executed.

In an operational effect of the invention in this embodiment, the stopper after the completion of the main work of preventing a piercing prior to the opening of a weak seal, which would otherwise be discarded, can be utilized for a secondary use, as is, for prevention of separation of an infusion set during execution of an infusion process, resulting in an increased safety of a infusion process and in an effective use of a resource.

BEST MODE FOR PRACTICING THE INVENTION

In FIGS. 1 to 5, a sealed medical liquid storage includes a medical bag 10 of flat shape and an outlet port 12. The medical bag 10 is made of a soft film (flexible material in the present invention) usually intended for a medical use, such as polyethylene or polypropylene of a thickness of, for example, 200 micron meter. The polypropylene films are, at its outer periphery, subjected to a pressing at a high temperature, such as 120° C. sufficiently higher than its softening temperature, so that a strong seal portion 14 is created, thereby forming a rectangular bag shape. Formed at the strong seal portion 14 is a suspension hole 16, by which the medical bag is held by a dripping stand, et al, thereby effecting intravenous dripping or dialyzing operation.

A weak seal portion 18 extends along the entire width of the medical bag 10 at a middle location in the longitudinal direction of the bag. At the weak seal portion 18, the front and rear surfaces of the medical bag are adhered, so that an inner space of the medical bag 10 is divided into a first compartment 20 and a second compartment 22. A first medical liquid is stored in the first compartment 20 and a second medical liquid is stored in the first compartment 22. The weak sealed portion 18 is created by pressing the front and rear polypropylene films constructing the medical bag 10 at a low temperature, such as 110° C., slightly higher than its softening temperature. Under a condition that respective medical liquids are stored in the first and second compartments 20 and 22, the medical liquids in the bag 10 are pressed from the outside, so that the weak seal portion 18 is broken and opened while the strong seal portion 14 being kept closed, result in a mixing of the first and second medical liquids. The term weak seal portion according to the present invention includes any fragile seal sealed portion, whereat an instantaneous fluidal communication from a closed condition is obtained.

The outlet port 12 is formed as a molded part from a plastic material such as a polypropylene of a thickness, which is enough to obtain a desired rigidity for making it possible to keep its intended shape. In order to obtain a desired adherence ability with respect to the medical bag 10, the outlet port 12 is desirably made of the same kind of plastic material as that of the medical bag 10 is used. As shown in FIG. 2, the outlet port 12 is formed with a cylindrical shape opened at its top and bottom. The outlet port 12 has a middle tapered portion 12-1 and a flange portion 12-2 at its end. A polypropylene cap 12-3 is contacted and welded to the flange portion 12-2. At the bottom surface, the cap 12-3 is formed with an opening, to which an inner rubber rid 12-4 is connected. During an intravenous dripping, the rubber inner rid 12-4 is pierced by a needle 24 of infusion set, so that the space inside the medical bag 10 is made communication with respect to an intravenous dripping line 26, so that an intravenous dripping is made possible. The plastic films constructing a top and a bottom surfaces of the medical bag 10 are subjected to a heating so that these surfaces are tightly contacted via a tubular portion of the outlet port 12, thereby obtaining a sealed structure of the medical bag 10 with respect to the outlet port 12.

In FIG. 1, a reference numeral 28 denotes a stopper for preventing a discharge of medicine according to the first embodiment of the present invention. The stopper 28 is adapted for preventing any access of a needle of an infusion set to the outlet port 12 when a weak seal portion 18 of the medical back is under non-opened condition. The stopper 28 is formed as a molded product from a plastic material such as ethylene, polypropylene or polystyrene of a value of rigidity and/or thickness, which is large enough for preventing the stopper to be pierced by a needle. As shown in FIG. 6, the medicine discharge stopper 28 has first and second portions, which are releasable and which are shown by a reference numeral 29 and construct a plurality of portions or a pair of portions in the present invention. The first and second portions 29 are, each, constructed by a rectangular shaped first flap and a similar rectangular shaped second flap 32. The first and second flaps 30 and 32 construct contacting portions in the present invention. As shown in FIG. 6, the first and second flaps 30 and 32 are, at their peripheries along bottom and side ends, beveled or tapered. The first and second flaps 30 and 32 are integrally connected to split halves of a tubular body having a tapered intermediate part and a closed cap shaped end. FIG. 3 illustrates, in a transverse cross-section, a combined or connected state of the halves, between which a space 34 is delimited. The space 34 has a shape, which is complimentary with respect to the shape of the outlet port 12, which allows the outlet port to be neatly stored in the space 34. As a result, even if a piecing of the inner rubber rid 12-4 of the outlet port 24 by a needle 24 of an infusion set were tried as shown in FIG. 2, the needle 24 is, at its pointed end, blocked by the stopper 28, so that an introduction of the needle 24 is unable.

Now, a half split structure 29 extending integrally from the first or second flap 30 or 32 will be explained. In FIG. 6, the first flap 30 is connected, via an intermediate portion 30-1, to a split tubular portion 30-2 as tapered and a split cap portion 30-3. Similarly, the second flap 32 is connected, via an intermediate portion 32-1, to a split tubular portion 32-2 as tapered and a split cap portion 32-3. As shown in FIG. 3, the split intermediate portions 30-1 and 32-1, the split tubular portions 30-2 and 32-2 and split cap portions 30-3 and 32-3 are recessed at their respective inner surfaces. When the first and second flaps 30 and 32 are end-to-end combined, these recess construct a space for storing the outlet port 12. Namely, the space has a shape, which is complimentary with the profile of the outlet port 12. As shown in FIGS. 3 and 4, the split cap portions 30-3 and 32-3 are connected with each other by an integral hinge 36 as a hinge means of movable parts in the present invention. As a result, the first and second flaps 30 and 32 are rotated between a closed condition in FIG. 3 and an opened condition in FIG. 4 about the integral hinge 36. In addition, the first and second flaps 30 are made one piece member, which results in a reduction in a number of part on one hand and, on the other hand, makes it possible to obtain the part by single die set, thereby reducing a molding cost. In FIG. 6, the split tubular portion 30-2 is, at a location adjacent the connector portion 30-2, provided with a somewhat thickened band-shaped portion 30-2A along the entire length (half way) in the circumferential direction of the split tubular portion 30-2. Furthermore, from the thickened portion 30-2A, a pair of cantilever fashioned portions 38 are integrally extended partially along the same circumference. The pair of cantilevered extended portions 38 form a resilient connecting means for connecting the first and second flaps 30 and 32 with each other under a predetermined resilient force. In the second flap 32, the split tubular portion 32-2 located adjacent the intermediate portion 32-1 is formed with an engaging grove 40 along the entire length (half way) in the circumferential direction. To the engaging groove 40 in the second flap 32, the cantilevered extended portion 38 extending from the first flap 30 is received in a manner that the first and second flaps 30 and 32 are connected with each other under a predetermined resilient force.

FIG. 3 illustrates a condition where the weak seal portion is non-opened (closed) condition, wherein medical liquids are separately stored in the compartments 20 and 22, respectively. Therefore, the medical bag 10 are expanded at a degree corresponding to the amount of the medical liquids stored in the chambers 20 and 22, respectively. The outlet port 12 is connected to the strong seal portion 14 of the medical bag 10 in a manner that the outlet port 12 is opened to the compartment 22. The outlet port 12 is, however, covered by the stopper 28. Namely, the first flap 30 is contacted with an upper side of the medical bag 10 (FIG. 1) and the second flap 32 is contacted with the lower side of the bag. The first and second flaps 30 and 32 are connected with each other via the medical bag, so that the medical bag 10 is substantially flattened between the first and the second flaps 30 and 32 as shown in FIG. 3. Namely, the medical liquid is properly loosely filled in the compartment 22. Therefore, even if the medical bag is flatly collapsed between the first and second flaps 30 and 32, the medical liquid can be completely flown to the remaining part of the compartment 22. Furthermore, the outlet port 12 is stored in the space 34 between the intermediate portions 30-1 and 32-1 connected to the first and second flaps 30 and 32, respectively, between the split tubular portions 30-2 and 32-2 and between the split cap portions 30-3 and 32-3 in a manner that the needle 24 is blocked by the plastic stopper 28. Thus, the inner rubber rid 12-4 in the outlet port 12 is prevented from being accessed and pierced by the needle. Furthermore, the pair of cantilevered fashioned parts 38 in the side of the first flap 30 is extended to and received by the groove 40 so as to hold the second flap 32 along substantially entire circumference. As a result, the resiliency of the cantilevered parts 38 opposes the first and second flaps 30 and 32 from being rotated along the hinge portion 36 in the direction as shown by arrows a in FIG. 6, thereby preventing the stopper 28 from being accidentally opened.

In order to cause the medical bag 10 to be opened, it is rested on a desk et al under a flat condition as shown in FIG. 3 and the palm of an operator such as a nurse is pressed from the above as shown by an arrow b. Although it is shown that the pressing of the medical bag 10 is done on the side of the compartment 20 in FIG. 3, the medical bag 10 may also be pressed on the side of the compartment 22 or even on both sides. Such a pressing of the medical bag 10 causes a hydraulic pressure to be applied to the weak seal portion 18, and, when a predetermined pressure is obtained, weak seal portion 18 is broken and opened or separated in a second. When the weak seal portion is opened, a pressure increased in the medical bag 10 by the pressing is instantaneously released, thereby generating a rushed or impact-like flow of medical liquid in the medical bag 10. In FIG. 4, such a rushed flow of medical liquid generated in the medical bag 10 is schematically illustrated by an arrow F. The rush of the medical liquid flow F in the medical bag 10 as generated upon the opening of the weak seal 18 urges the medical bag 10 to be expanded at the location where the latter is contacted with the first and second flaps 30 and 32. As a result, the first and second flaps 30 and 32 contacting the opposite surfaces of the medical bag urged to be expanded are now rotated outwardly (the direction of the rotating movement of the flaps 30 and 32 are illustrated by arrows a in FIG. 6) about the hinge portion 36 as shown in FIG. 4 against the resilient force generated by the engagement of the cantilevered extended portion 38 with the groove 40, so that the portion 38 is separated from the groove 40, resulting in the removal of the stopper 28 from the outlet port 12. Thus, the outlet port 12 is exposed outwardly, which allows the rubber rid 12-4 to be accessed and pierced by needle 24 of infusion set, thereby permitting the intravenous dripping operation to be initiated.

In this embodiment of the present invention, an erroneous operation that the intravenous dripping is practiced under a non-opened condition of the medical bag does not likely, since the outlet port 12 of the medical bag 10 is covered or blocked by the stopper 28. Furthermore, the opening of the medical bag 10 by the breakage of the weak seal 18 causes the stopper 28 to be automatically released from the outlet port 12 of the medical bag 10 under the action of the first and second flaps 30 and 32 operated by the rapid expansion of the medical bag 10 at the instant of the breakage of the weak seal portion 1-8, which allows an intravenous dripping operation by the medical bag 10 after its opening to be smoothly practiced.

FIGS. 7 and 8 illustrate second embodiment of a sealed storage for medical liquids of mixed type, which includes a stopper 128 for preventing a discharge of medical liquid from a medical bag 10. The stopper 128 includes a first flap 130 of a rectangular plate shape and a second flap 132 of a rectangular plate shape, contacting with opposite faces of the medical bag 10, respectively. The first and the second flaps 120 and 132 are connected to half parts 130-1 and 132-1 of a shape of a tubular body. FIG. 7 shows, in a side view, the split parts 130-1 and 132-2 in their combined state. In this combined state, between the split parts 130-1 and 132-2, a chamber 134 is created, in which the outlet port 12 is stored at an end located adjacent the medical bag 10. In this embodiment, the outlet port 12 is provided with a cap portion 12-3, which is outwardly opened. As a result, in this embodiment, a piercing of a needle 24 of infusion set into the inner rubber rid 12-4 is possible. However, even if the needle 24 is pierced, the stopper 128 can prevent the discharge of medical liquid from being occurred so long as the medical bag 10 is non-opened condition. Namely, the medical bag 10 is flatted and closely contacted with each other at their opposed surfaces by the first and second flaps 130 and 132 of the stopper 128. The closely contacted portion of the opposite surfaces of the medical bag 10 is illustrated by a reference numeral 10' in FIG. 8. Such a closed contacted portion 10' of the medical bag 10 prevents the medical liquid therein from being flown toward the outlet port 12.

In this embodiment, the function of the first and second flaps 130 and 132 is such that the upper and lower opposite faces of the medical bag 10 are closely contacted at an area along the entire periphery around the opened portion of the outlet port 12. In order to obtain this function, the flaps 130 and 132 are provided with portions extending from the outer periphery of the medial bag, between which portions the outlet port 12 is arranged and which portions are connected with each other by a weak connecting portion 140, which is capable of broken under an outside force according to the present invention. Such a weak connecting portion 140 may be constructed by the half split portions 130-1 and 132-1, which are, at their faced ends, weakly welded or adhered. The weak connector portions 140 are arranged on opposite sides in contacting parts between the first and second flaps 130 and 132 in a manner that the faced parts 10' of the medical bag 10 contacting the first and second flaps 130 and 132 are substantially flatly and closely contacted with each other. As a result, under a normal two-liquid condition where the medical liquids are separated by the non-opened (closed) weak seal 18, the medical liquids in the medical bag 10 are blocked by the closely contacted portion 10' and are prevented from being flowing toward the outlet port 12. Therefore, a piercing of a needle of an infusion set to the inner rubber rid 12-4 of the outlet port 12 is, itself, possible, which, however, does not allow any intravenous dripping to be practiced.

When the weak seal portion 18 is opened, the medial bag is subjected to a pressing so that a hydraulic pressure applied to the weak seal 18 is increased to a predetermined value, which causes the weak seal 18 to be instantaneously broken and opened. As already explained with reference to the first embodiment with reference to FIG. 4, the breakage of the weak seal 18 causes the increased pressure to be instantly discharged, resulting in a generation of a rushed flow of the medical liquid in the medical bag 10. As already explained with reference to FIG. 4, such a rushed flow of the medical liquid generated in the medical bag 10 causes the medical bag 10 to be widened at a location where the bag 10 is contacted with the first and second flaps 130 and 132. The first and second flaps 130 and 132 contacting the opposed surfaces of the widened medical bag 10 are moved as shown by arrows h, resulting in a breakage of the weak connector portion 140, thereby separating the stopper 129. As a result, the closed contact of the opposite layers of the medical bag at an opened portion of the outlet port 12 to the inner space of the medical bag is cancelled, so that the medical liquid is flown toward the outlet port 12, thereby allowing out an intravenous dripping operation to be carried out by a infusion set.

In the above embodiment, in order to construct the weak connected portion 140, the first and second flaps 130 and 132 are glued by an adhesive et al at the faced portions. Such a weak connected portion 140 normally closely connects the opposed surfaces of the medical bag 10. However, when the medical bag 10 is opened, the weak glued portions are broken, so that the first and second flaps 130 and 132 are mutually rotated in the directions as shown by arrows h in FIG. 7 and separated from the medical bag 10. In place of the use of a temporal adhesive, a permanent type connector provided with perforations can be used for combining the first and second flaps 130 and 132 with each other. Such a perforation allows the permanent type connector to be mechanically broken when the medical bag is opened.

In the first embodiment shown in FIGS. 1 to 6, a connection between the first and second flaps 30 and 32 may be carried out by a weak connector, which is able to be broken under an outer widening force as similar to those in FIG. 7 and 8. Furthermore, in the second embodiment in FIGS. 7 and 8, in order to prevent the flow of medical liquid to the outlet port 12, the top and bottom layers of the medical bag 10 may be closely contacted by the first and second flaps 130 and 132 under a resilient force as similar to the embodiment in FIGS. 1 to 6.

In the first and second embodiments of the present invention, the stopper 28 or 128 blocks the outlet port 12 of the medical bag 10, thereby preventing any occurrence of erroneous operation that an infusion operation is carried out under an non-opened condition of the medical bag. In addition, the stopper 28 is removed from the outlet port 12 of the medical bag 10 by the provision of the first and second flaps 30 and 30, which are driven by the instantaneous expansion of the medial bag 10 at the instance of the opening of the weak seal 18, which allows the execution of infusion operation to be smoothly initiated after the opening of the medical bag 10.

FIGS. 9 to 17 illustrates a stopper 228 of third embodiment of the present invention. In this embodiment, in addition the originally intended function of a blockage of a piercing of a needle of an infusion set during a non-opened condition of the medical bag, the stopper 228 is devised so that the latter has a function of holder for holding the needle with respect to the medical bag after the opening of the medical bag. As shown in FIG. 9, the stopper 228 is provided with a pair of parts, which are respectively provided with first and second flaps 230 and 232 as contacting portions in the present invention. The first and second flaps 230 and 232 integrally linked to parts 231 and 233 as split halves of a tubular body, which split halves are shown under a combined state in FIG. 11, between which halves a chamber 234 is formed. The chamber 234 has a shape, which is complimentary with that of the outer profile of the outlet port 12. Thus, the outlet port 12 can be neatly stored in the chamber 234.

In this embodiment, during normal operating mode of the stopper 228 for preventing a piercing of an infusion set to the outlet port 12 of a medical bag under non-communicated condition, a the first and second flaps 230 and 232 and the split bodies 231 and 233 are respectively rigidly linked with each other. A linkage means for attaining this function is shown in FIG. 11 and, under an enlarged scale, in FIG. 14. As shown in FIG. 14, the linkage means 251 includes portions 230A and 232A of a hook shaped cross section and extending along a circumferential direction of an angle of 180 degree at ends of the first and second flaps 230 and 232, respectively and portion 231A and 233A of a hook shaped cross section and, also, extending along a circumferential direction of an angle of 180 degree at ends of the split half portions 231 and 233, respectively. The portions 230A and 232A have cross sectional shapes in a transverse cross-section, which are complimentary with those of the portions 231A and 233A. Thus, an engagement of the portion 230A and 231A of complimentary shapes is possible, which allows the first flap 230 to be substantially rigidly linked (connected) with the split half portion 231, so that substantially half split tubular inner space S1 is created. In similar way, an engagement of the portion 232A and 233A of complimentary shapes is possible, which allows the second flap 232 to be substantially rigidly linked with the split half portion 233, so that substantially half split tubular inner space S2 is created. Thus, as shown in FIGS. 9 and 11, on one side of the medical bag, the first flap 230 is rigidly connected (linked) with the half split portion 231 and, on the opposite side of the medical bag, the second flap 232 is rigidly connected with the half split portion 233. In short, the stopper 228 is constructed from a pair of rigid half parts, between which the medical bag 10 is arranged.

In this embodiment, the stopper 228 is intended also for obtaining a function of a holder of needle during the execution of an infusion operation. Namely, the stopper 228 is, as shown in FIG. 11, formed with a chamber 250 at an end remote from the medical bag 10, which chamber is opened outwardly via an opening 252 at the end of the stopper 228. A needle is stored in the outwardly opened space 205 so as to obtain a function of a holder for preventing a removal of the needle. In order to prevent the outlet port 12 from being pierced during non-communicated condition of the medical bag regardless of the above mentioned opened structure, the split halves 231 and 233 are, at their inner walls, formed with circumferential grooves 254 along the entire lengths. The circumferential grooves 254 are clearly illustrated in FIGS. 12 and 15. Under the combined condition of split tubular portions 231 and 233, the circumferential grooves 254 are cooperated so as to extend substantially along 360 degree. Fitted to the grooves 254 is a needle blockage disk 260 made of a certain hard material, which disk functions as a blocking member of the present invention. As shown in FIG. 11, the needle stopper disk 260 is located adjacent to and outwardly from the cap 12-3 under the condition of the stopper 228 mounted to the outlet port 12 of the medical bag 10. As a result, a needle is blocked by the disk 260 even when introduced into the chamber 250 via the opening 252, and, thus, the rubber rid 12-4 (FIG. 17) is prevented from pierced by the needle. Thus, the function of the stopper 228 for preventing the piercing during non-opened condition is obtained. As shown in FIG. 9, the split tubular portions 231 and 233 are provided with circumferential openings 262 and 264, so that a tamper seal member (not shown) attached to the outlet port 12 at the location of the rubber rid is freely passed.

Next, a resilient connecting means for connecting the split halves 231 and 233 with each other under a predetermined resilient force will be explained. A pair of notches 238 are integrally extended from a split end surface of the first split half tubular body 231. A pair of box shaped catches 240 are provided on a split end surface of the second split half tubular body 233. As shown in FIG. 13(a), each of box shaped catches 240 is formed with a space of rectangular shape having a bottom wall formed with an engaging piece 272 having a front portion slightly rearwardly inclined. As a result, when the split tubular portions 231 and 233 are contacted at their split end surfaces, i.e., when the split portions 231 and 233 are moved toward each other in a direction shown by an arrow f in FIG. 13(a), the notches 238 are received by the respective catches 240. During such movement, initially, leading ends 238A of the notches 238 displace the respective engaging pieces 272 slightly downwardly against the spring force, and, finally, a condition as shown in FIG. 13(b) is obtained, where the leading ends 238A of the notches 238 climb over the engaging pieces 272. In this final condition, where an engagement of the leading ends 238A and the engaging pieces 272 is obtained, the split portions 231 and 233, in other words, the first and the second flaps 230 and 231 are united under a predetermined resilient force as shown in FIG. 9.

Next, an operation of the stopper 228 will be explained in its function for blockage of the piercing during a non-opened condition of a medical bag. Namely, FIG. 11 illustrates a condition where the weak seal 18 of the medical bag 10 is under non-opened condition. Therefore, medical liquids are stored in the respective compartments 20 and 22 and the medical bag is under a slightly expanded for the amount of the medical liquids stored in the respective compartments 20 and 22. The split tubular parts 231 and 233 are combined so that the outlet port 12 of the medical bag 10 is between the parts 231 and 233 under a predetermined resilient force as generated by the resilient connector means constructed by the notches 238 and the catches 240 (FIG. 9). The combined or tied condition of the split tubular parts 231 and 233 by the resilient connector is shown in FIG. 13(b). Furthermore, the first flap 230 is contacted with one side of the medical bag 10 and the second flap 232 is contacted with the opposite side of the medical bag 10. In this embodiment, the stopper has an opening 252 at the outer ends the split tubular portions 231 and 233. However, this opened structure of the stopper does not allow the rubber rid of the outlet port 12 to be pierced by a needle of an infusion set due to the fact that needle is blocked by the disk 260 even if the needle is introduced into the space 252 via the opening 252.

In order to open the medical bag 10, as similar to the first embodiment as already explained with reference to FIG. 3, the medial bag 10 is, at a portion of the compartment 20 or 22, pressed by the palms of an operator from the above. Due to the pressing of the medical bag 10, a hydraulic pressure is applied to the weak seal 18, which causes the weak seal to be instantly broken and opened. An increased pressure in the medical bag 10 is instantly released and generates a rushed flow of medical liquid, which causes the medical bag 10 to be expanded at locations contacting with the first and second flaps 230 and 232, as shown in FIG. 12. The first and second flaps 230 and 232 contacting with the opposed layers of the medical bag as expanded are urged so that the flaps 230 and 232 are rotated about a hinge portion against the resilient force generated by an engagement of the notches 238 with the catches 272. As a result, the engagement of the notches 238 with the catches 272 is released and the flaps 230 and 232 are moved as shown by arrows a in FIG. 12, so that the split parts 231 and 233 constructing the stopper 228 are completely separated. As a result, the needle block disk 260 as previously fitted to the grooves 254 is completely disengaged from the grooves and separated. Due to the removal of the stopper from the outlet port 12, the latter is outwardly exposed, so that a piercing of a needle of an infusion set becomes possible, thereby allowing of an infusion operation to be started.

Unlike the stopper in the first or second embodiment where the stopper is wasted after the opening, the stopper 228 in the third embodiment features that it is also for used for holding a needle during the execution of an infusion operation, which will subsequently occurs. This feature will now be explained with reference to FIGS. 15 to 17. When an infusion operation is initiated, a medical bag 10 is, first, suspended from a stand by a suspension hole, which is not shown in FIG. 15 but formed at a strong seal 14 at an upper position in FIG. 15 opposite the outlet port 12 as similar to the suspension hole 16 in FIG. 1. Then, a needle 24 of an infusion set is pierced through the rubber rid 12-4 of the outlet port 12. FIG. 17 illustrates a condition that the needle 24 is pierced to the rubber rid 12-4 at a predetermined depth. On the other hand, the stopper 228, mounted to the outlet port 12 prior to the opening of the weak seal, is now separated as shown in FIG. 12 as a result of the execution of the opening of the weak seal, resulting in a removal from the medical bag 10. In this removed condition, the first and the second flaps 230 and 232 are separated from the split tubular portions 231 and 232, respectively. Namely, as already explained with reference to FIG. 14, the first flap 230 and the split half portion 231 are under a substantial rigid connection with each other by an engagement of the hook shaped cross-sectioned portions 230A and 231A of complimentary shapes. Therefore, a rotating movement of the first flap 230 with respect to the split half portion 231 causes the hook shaped cross-sectioned portions 230A and 231A to be subjected to a mutual slide movement, so that, after a relative movement of 180 degree, the split half portion 231 is separated from the first flap 230. In the similar way, the other split half portion 233 is separated from the second flap 232. By using such a pair of split half portions 231 and 233 from which the first and second flaps 230 and 232 are respectively separated, a holding operation of a needle 24 is obtained during an execution of an infusion operation. Namely, as shown in FIG. 15, a pair of the split half portions 231 and 233, from which the first and second flaps, respectively are separated, are arranged so that the portions 231 and 233 are opposed with each other, while the outlet port 12 is arranged between the portions 231 and 233. In this regard, the needle blocker 260 as was essential until the opening as shown in FIG. 11 is no longer needed. Thus, the circumferential grooves 254 for an installation of the needle blockage disk 260 in the condition in FIG. 11 is now freed as shown in FIG. 15. When the split half portions 231 and 233 are to be combined with each other, the notches 238 on one side (231) is engaged with the catches 240 under a resilient force in the similar way as explained with reference to FIGS. 13(a) and (b). FIG. 16 shows a combined condition between the split half portions 231 and 233 after the removal from the first and second flaps 230 and 232, where the connected or linked portions with the removed first and second flaps 230 and 232, i.e., the ends surfaces of the hook shaped portions 231A and -233A are located slightly below the lower edge of the strong seal 14 of the medical bag 10. In this combined condition of the split half portions 231 and 233 as shown in FIGS. 16 and 17, a body portion 24-l of the needle 24 is passed through the opening 252 at the ends of the split halves 231 and 233 as tied and a connecting portion 24-2 to the needle 24 is housed in the space 252 formed by the combined split halves 231 and 233. Furthermore, a flange 24-3 at the end of the body portion 24-1 is engaged with an edge of the opening 252 formed by the combined split halves 231 and 233. Furthermore, since the split halves 231 and 233 are combined at a predetermined resilient force due to the engagement of the notches 238 with the catches 240, the needle 24 is held in a manner that a removal of the needle from the exhaust port 12 does not occur during the execution of the infusion operation even if the needle is stretched and slightly overly stressed. This function contributes to obtain safer working in an infusion operation.

FIGS. 18 and 19 illustrates a fourth embodiment of a stopper 328 of the present invention. As similar to the third embodiment, in addition to the originally intended function of blockage of piercing by a needle of an infusion set during non-opened condition of the medical bag, the stopper 328 of this embodiment has an additional function of a holder of a needle with respect to the medical bag after the opening of the medical bag 10. Namely, the stopper 328 is formed with a pair of parts astride the medical bag 10, which parts are provided with first and second flaps 330 and 332, respectively, as contacting parts of the present invention. The first and second flaps 330 and 332 are integrally connected (linked) to split portions 331 and 333 of shapes cut from a tubular body by a linkage means 351 similar to the linking means 251 shown in FIG. 14 in reference to the third embodiment. The second split half portion 333 is, at its end, formed integrally with a holder portion 370 of generally U shape for holding an infusion set. The first split half portion 331 terminates as end surface 331A at a location adjacent the circumferential groove 354 (FIG. 19) for an insertion of a blocker disk 360. The holder portion 370 of U shape at the end of the second split half portion 333 extends in a cantilever fashion in a manner that the holder portion 370 locates adjacent the end surface 331A of the first split half portion 331.

The stopper 338 of the fourth embodiment operates in similar way as the third embodiment does. Namely, a first and second split portions 331 and 334 are arranged so that the outlet port 12 of the medical bag 10 is arranged between the portions 331 and 334, which are tied under a predetermined resilient force generated by a resilient connecting means constructed by latches 338 and catches 340 and a piercing by a needle of an infusion set is prevented by a disk 360 arranged in circumferential grooves 354 in the split portions 331 and 334.

As similar as explained with reference to the third embodiment in FIG. 12, the first and second flaps 330 and 332 receive an instantaneously increased (impact-like) pressure upon the opening of the medical bag 10, so that the flaps are widened, which causes the latches 338 to be disengaged from the catches 340. As a result, as similar to the first to third embodiments, the split half portions 331 and 332 are separated from each other, resulting in a release of the needle block disk 360 from the grooves 354 in the split half portions 331 and 332, which allows a needle of an infusion set to be pierced for stating an infusion operation.

In order to allow a needle to be held during the working of infusion, the first and second flaps 330 and 332 of the stopper 328 are separated as shown in FIG. 19, as similar to the third embodiment as explained with reference to FIG. 14. Then, a needle 24 can, now, be pierced to a rubber rid 12-4 of the outlet port 12 and the split parts 331 and 334 are tied. In this tied condition, the needle holder portion 370 of U shape in the second split half portion 333 extends at a location below the flange portion 24-3 in a manner that the U-shaped portion 370 holds the body portion 24-1 of the infusion set while the first split half portion 331 is combined and locked with the second split half portion 333 by an engagement of the latches 338 with the box shaped catches 340. In this locked condition, the flange 24-3 of the needle 24 is engaged with an inner shoulder portion 328' of the stopper 328 while the flange 24-3 of a needle 24 is engaged with a boom portion 370A of the holder portion 370, which hold the needle so that a removal from the outlet port 12 is prevented. In this forth embodiment, the infusion set can be held only by the second split half portion 333, due to the fact that the U-shaped holder portion 370 of the second split half portion 333 extend in a manner that it embraces the body portion 24-1 of the infusion set.

In the above explained third and forth embodiments, the originally intended function for preventing a piercing prior to the opening of the weak seal as same in the first and the second embodiments is maintained and, in addition, substantially the same construction of the stopper after the completion of the originally intended use can also be used for preventing a infusion set from being separated during the execution of an infusion operation, which is advantageous not only from the view point of a cost but also from the view point that an improved efficiency of infusion operation.

Through the above first to forth embodiments, it has been described that the medical bag 10 is a type that medical liquids are mixed. However, the present invention is realized in a medical bag of a type where a liquid is mixed with a medicine(s) other than liquid state, such as a powder state. Furthermore, an installation of a stopper according to the present invention can be made not only before but also after an introduction and sterilization of medical liquids. Furthermore, the present invention is applied to a medical bag having, in addition to an outlet port of medial liquid, a mixing and introduction port of medicine.

Throughout the first to fourth embodiments, it has been explained that the first and second flaps as contacting portions of the present invention are of a substantially rectangular plate shape. However, the present invention is not limited to this shape and has any desired shape, which allows the flap to receive a necessary hydraulic force and which prevents the flap from being accidentally opened when it is dropped. FIG. 20 illustrates examples of shape of the flap realized in the third embodiment. Namely, (a) shows a flap having an oblique edge 230-1, (b) shows a flap having stepped edge 230-2 and (c) shows a flap having a cut-out 230-3. The flap may have any other desired shape capable of obtaining a desired pressure receiving characteristic.

In the above, the resilient connecting means for connecting the first and second flaps under a predetermined force is constructed by an integral cantilever portion 38 (FIG. 6) in the first embodiment, a weak connecting portion by welding or adhesion (FIG. 7) in the second embodiment, a pair of notch 238 (FIG. 9) in the third embodiment and a pair of notch 338 (FIG. 18) in the fourth embodiment. The present invention is not limited to such construction. For example, split tubular portions from first and second flaps may be connected by a separate C-shaped stopper or by a tape wound around the portions. In addition, a shrink connector member may be used. Furthermore, split half portions are releasably connected with each other by a hook shaped resilient connecting member. In short, any construction may be employed, by which a desired degree of releasable connection (connecting force) is obtained. Finally, each of split halves may be constructed as a "hermaphrodite" body, where a cantilevered portion 38 and an engaging groove are, both, provided.

BRIEF EXPLANATION OF ATTACHED DRAWINGS

FIG. 6 is a perspective view of a stopper of a first embodiment of the present invention.

FIG. 7 is a side view of a medical bag in a second embodiment of the present invention.

FIG. 12 is a partial cross-sectional view of FIG. 11 at a location adjacent the outlet, which illustrates a separated condition of the stopper, when the medical bag is opened.

FIG. 13 is cross-sectional views taken along lines XIII-XIII in FIG. 10, illustrating in enlarged scale a resilient connecting means, where (a) illustrates a condition prior to the completion of a connection and (b) illustrates a condition after completion of the connection.

EXPLANATION OF SOME REFERENCE NUMBERS

Figure 1:
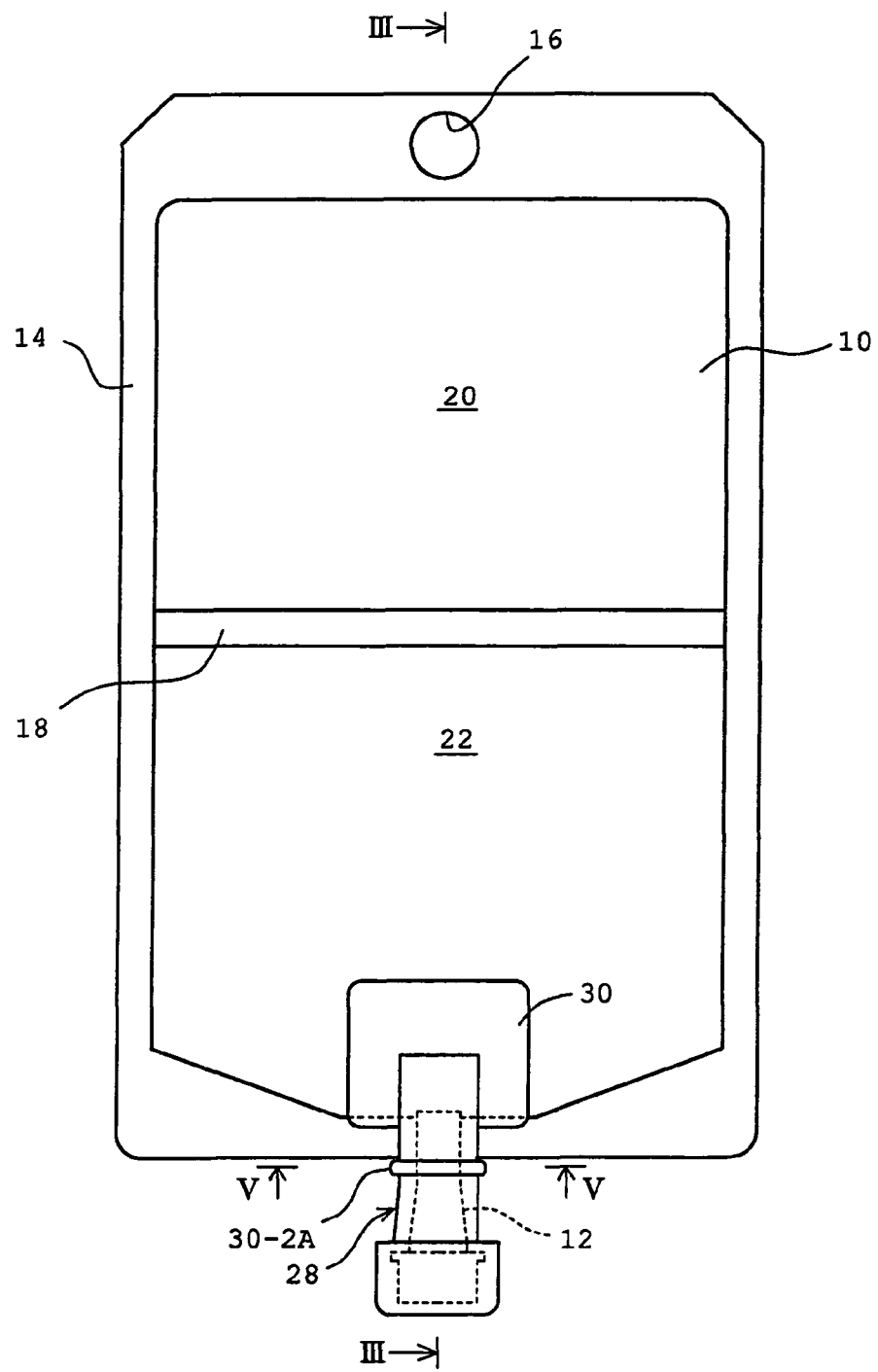
FIG. 1 is a plan view of a medical bag with a stopper according to the present invention, which is a view taken along an arrow I in FIG. 3.
Figure 2:
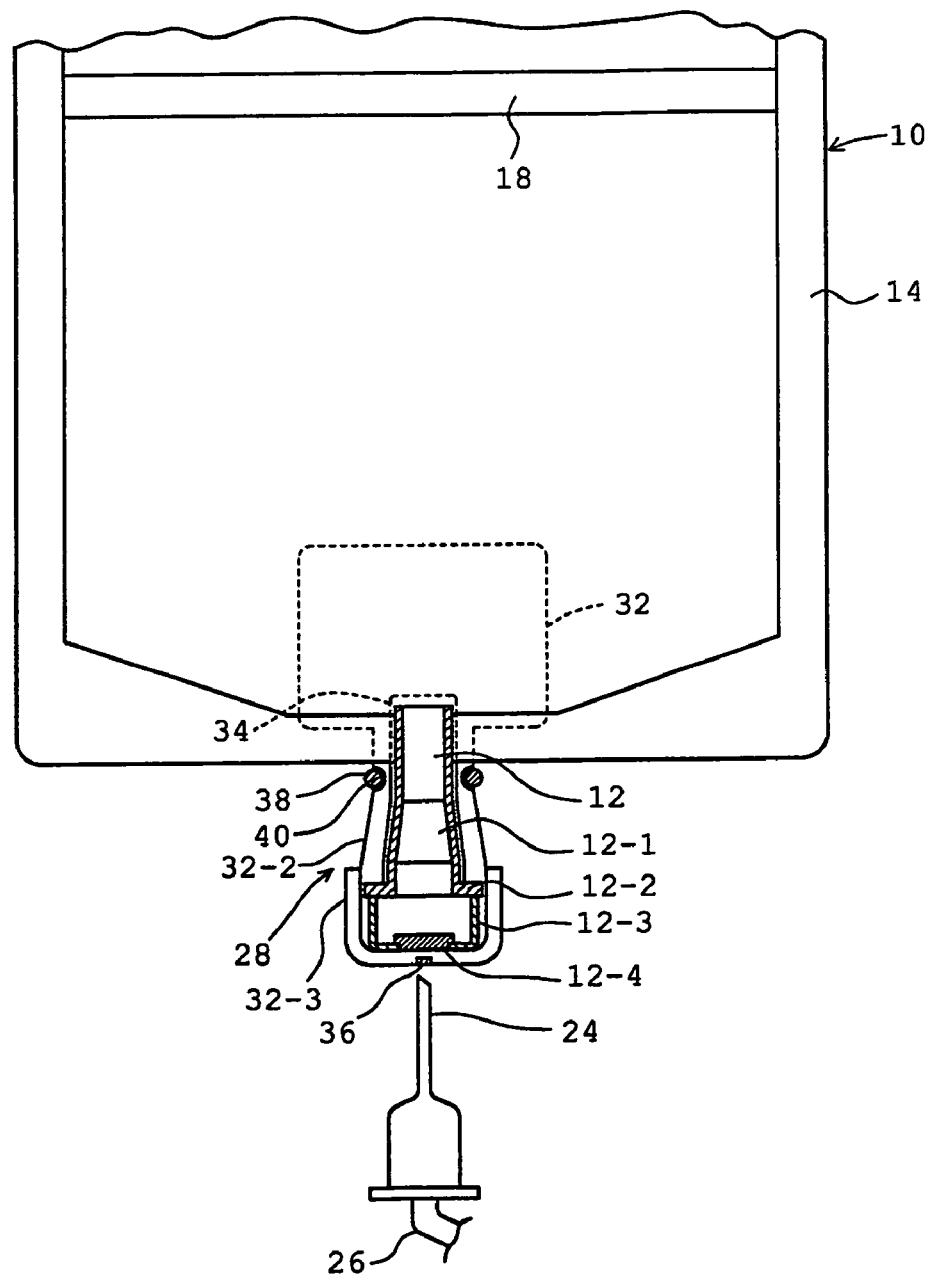
FIG. 2 is a detailed view of a portion of the stopper in FIG. 1, which is a view taken along lines II-II in FIG. 3.
Figure 3:
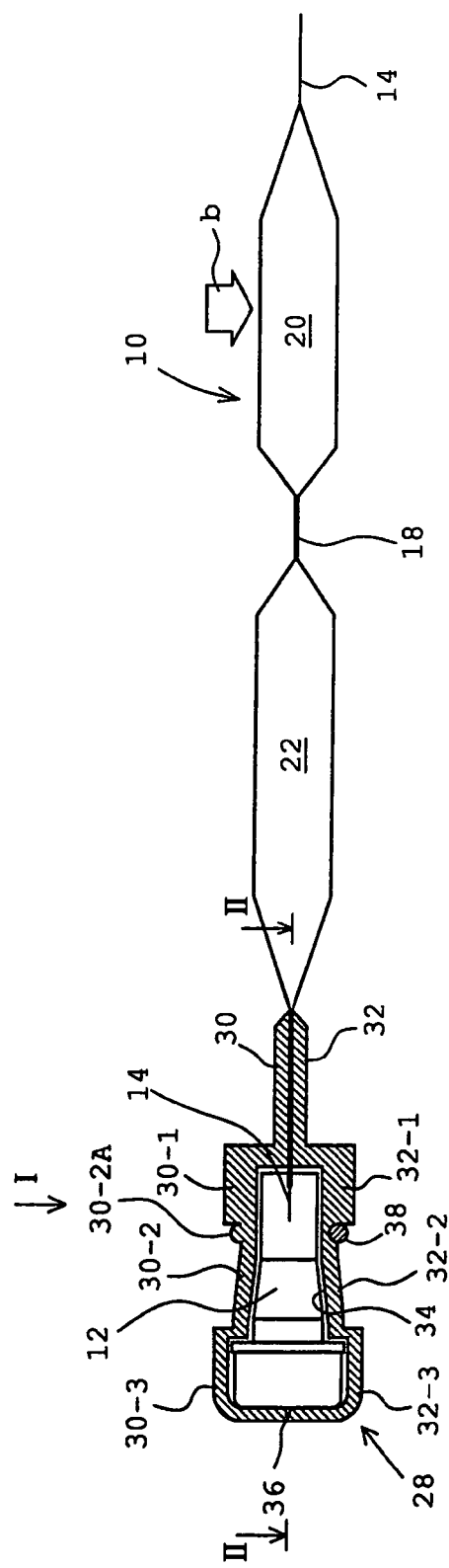
FIG. 3 is a longitudinal cross-sectional view of the medical bag with the stopper according to the present invention, which is a view taken along lines III-III in FIG. 1.
Figure 4:
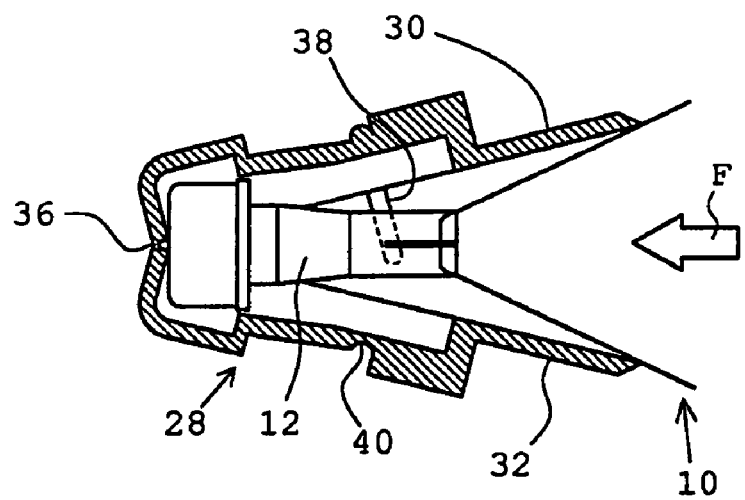
FIG. 4 is a partial cross-sectional view illustrating a separated condition of the stopper in FIG. 3, when the medical bag is opened.
Figure 5:
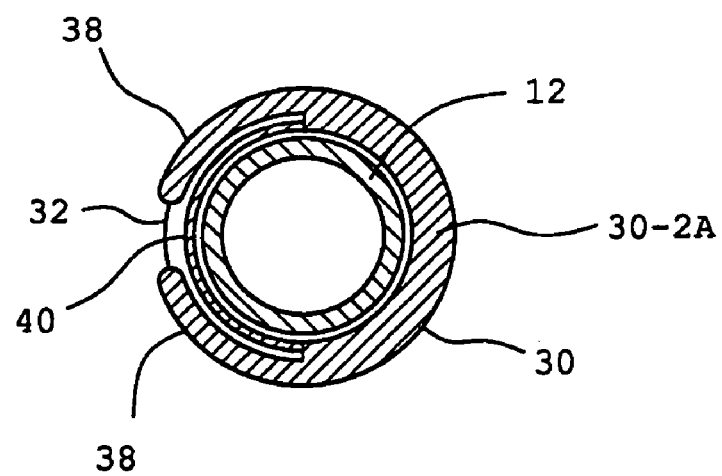
FIG. 5 illustrates a resilient means for uniting a first and second flaps, which is a cross-sectional view taken along lines V-V in FIG. 1.
Figure 8:
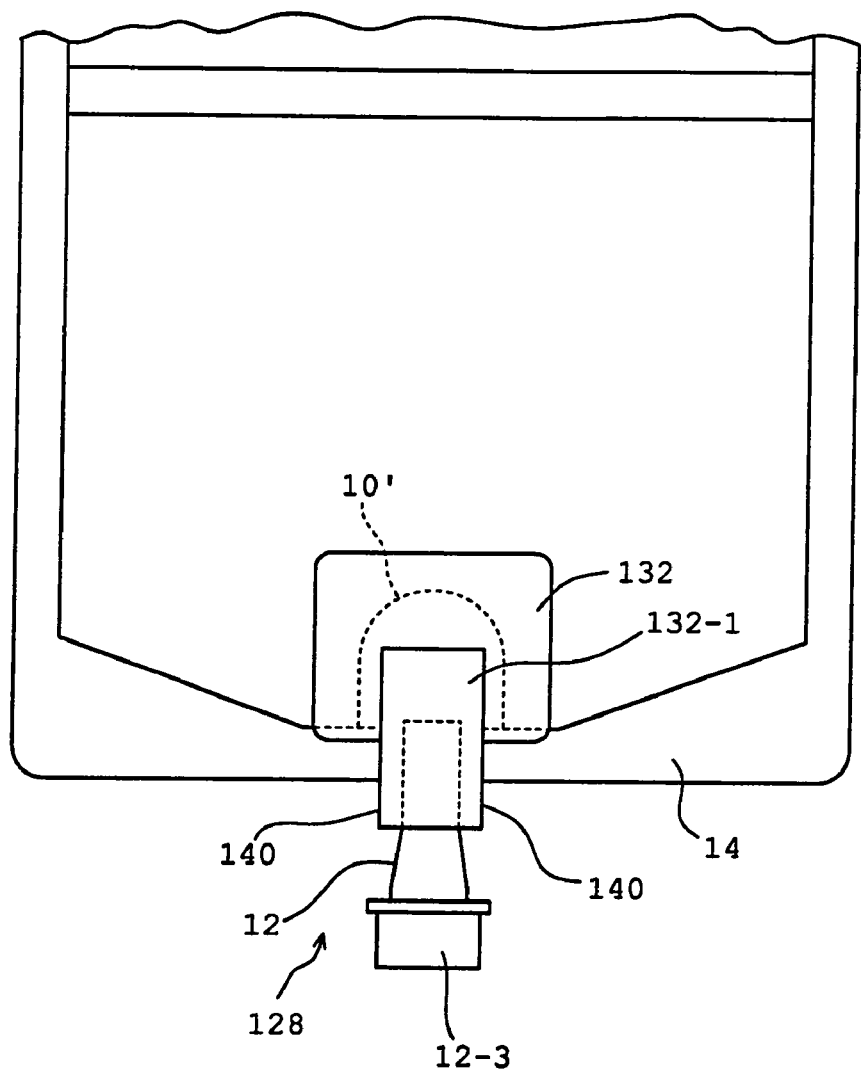
FIG. 8 is a plan view of the medical bag taken along line VIII-VIII in FIG. 7.
Figure 9:
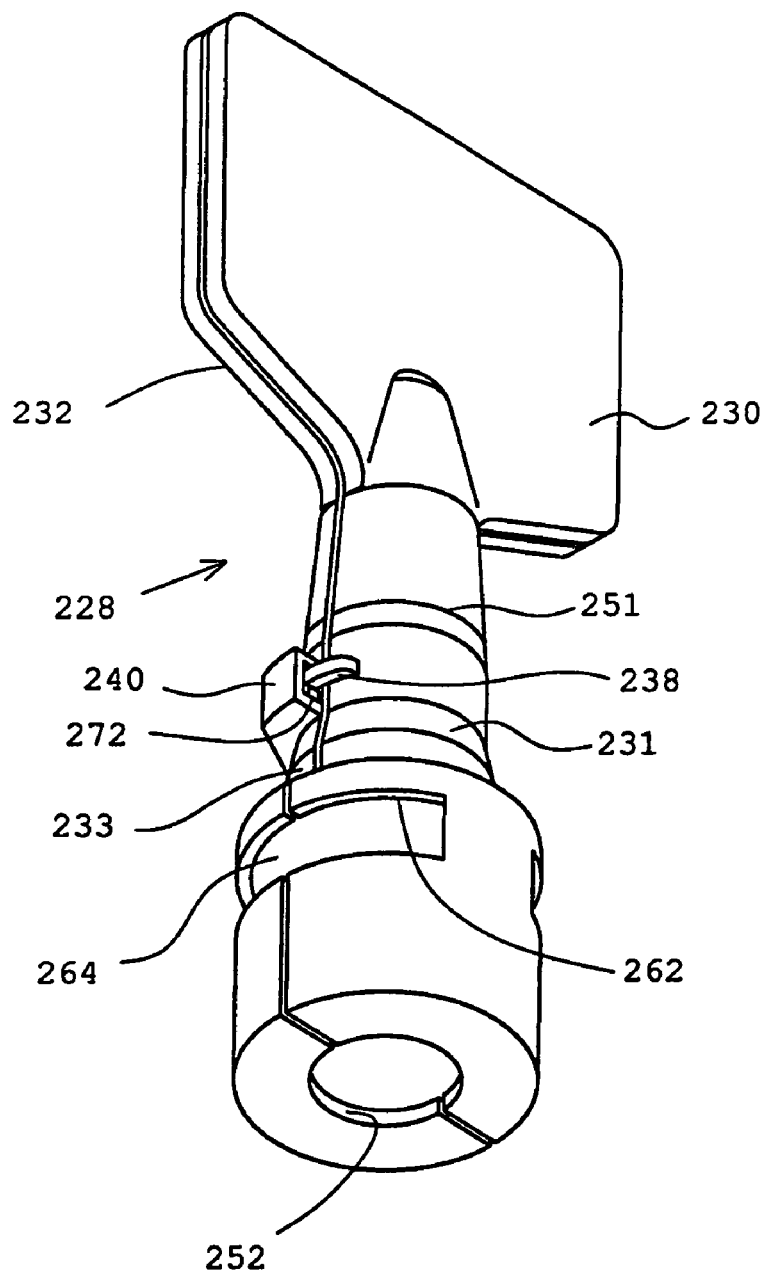
FIG. 9 is a perspective view of a stopper of a third embodiment of the present invention.
Figure 10:
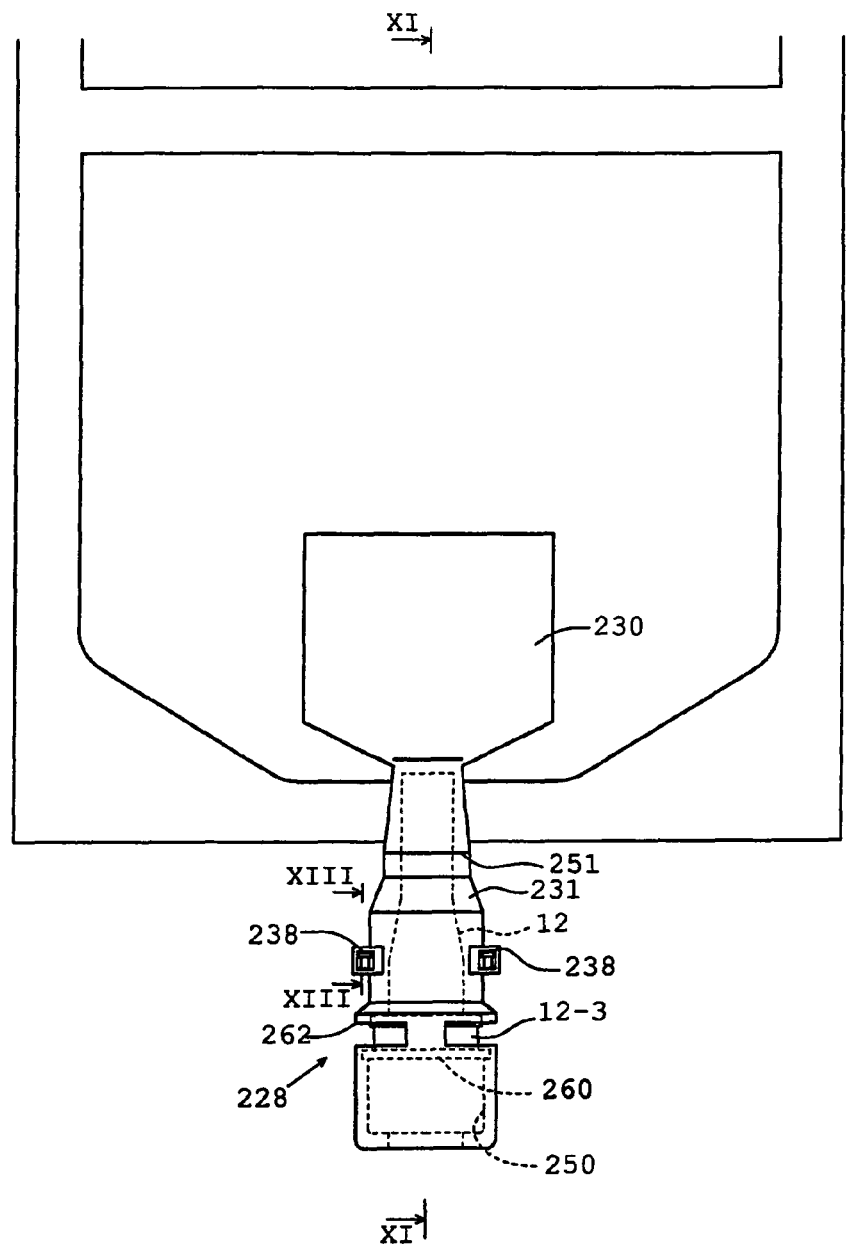
FIG. 10 is a plan view of a medical bag, to which the stopper in FIG. 9 is installed.
Figure 11:
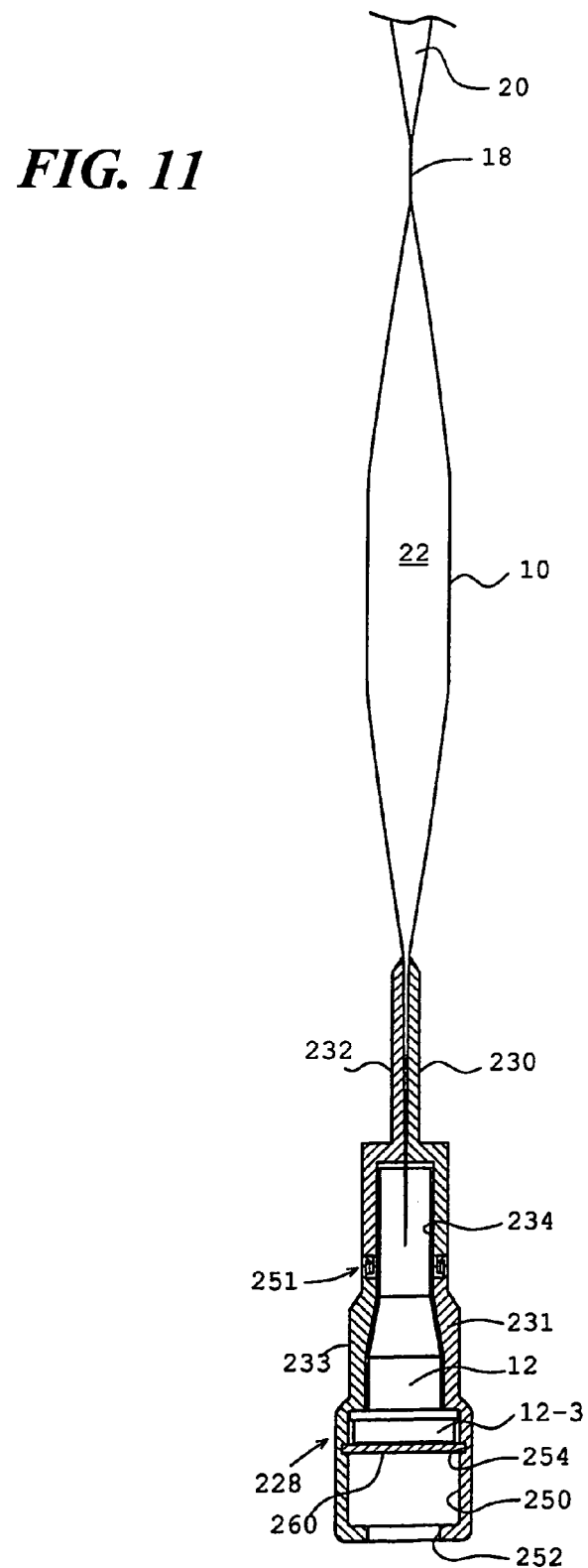
FIG. 11 is a longitudinal cross-sectional view of a medical bag, which is a view taken along lines XI-XI in FIG. 10.
Figure 14:
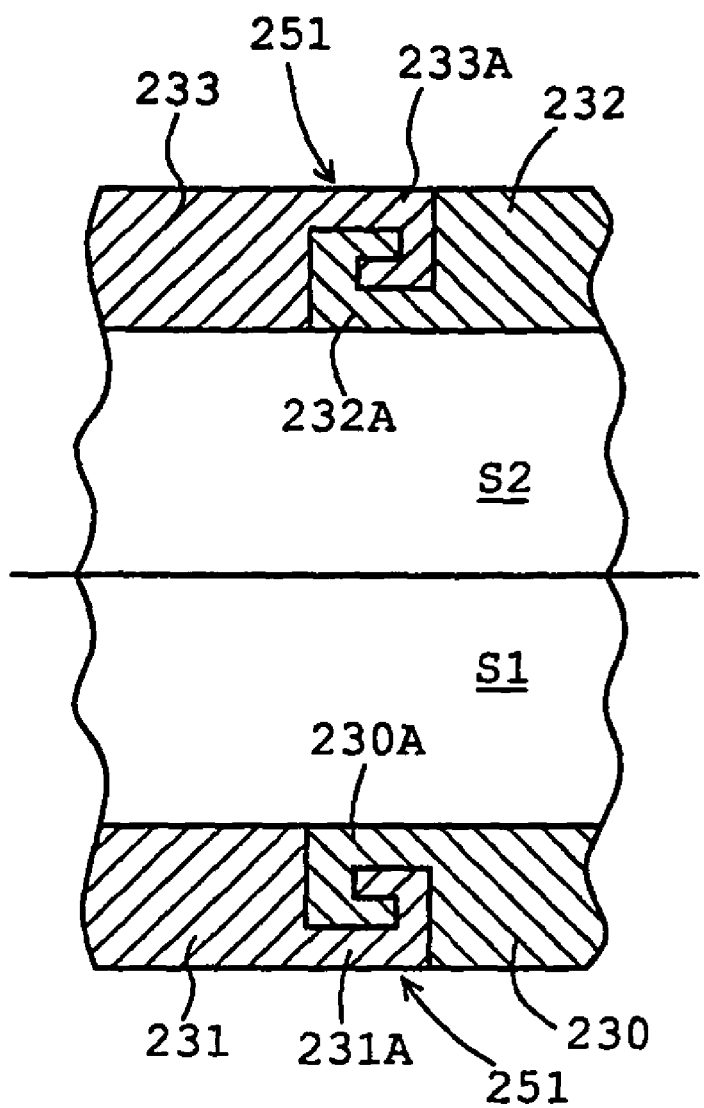
FIG. 14 is a partial enlarged view of FIG. 11 for illustrating in detail means for a rigid linkage of first and second flaps with split halve portions.
Figure 15:
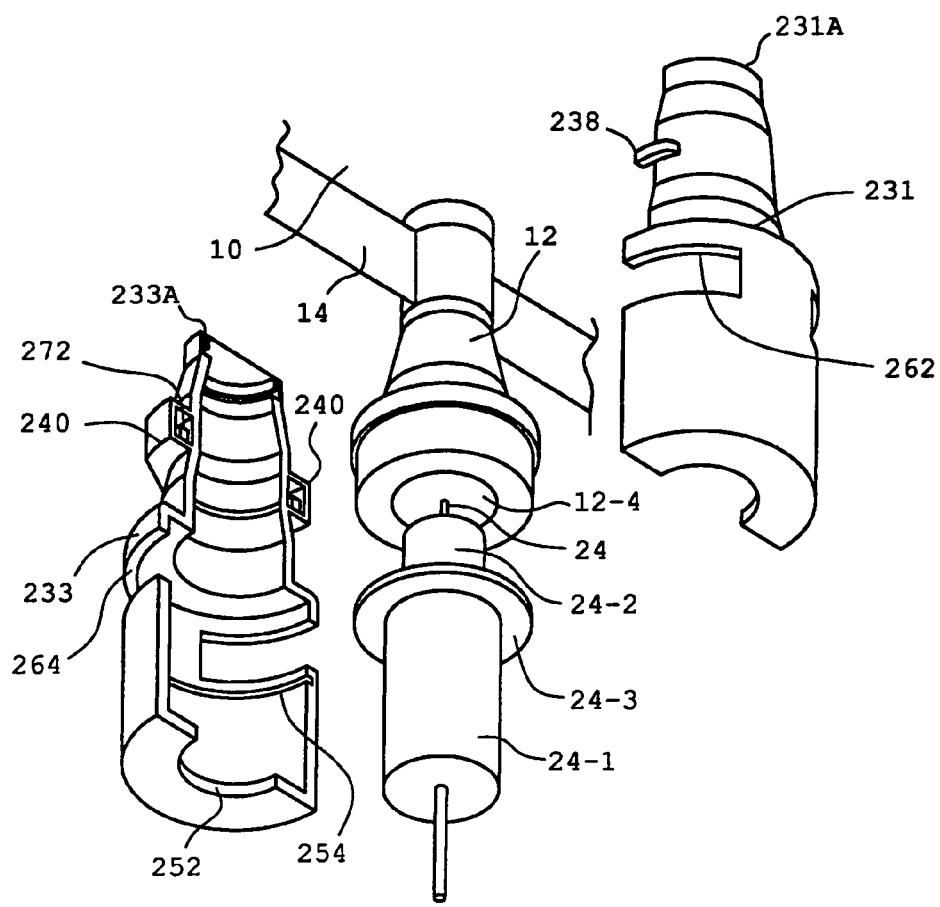
FIG. 15 is a perspective view of the split half portions under a separate state prior to an installation to the outlet port, when the stopper in FIG. 9 after removal of the first and second flaps is used for a holder for preventing a needle of infusion set from being removed.
Figure 16:
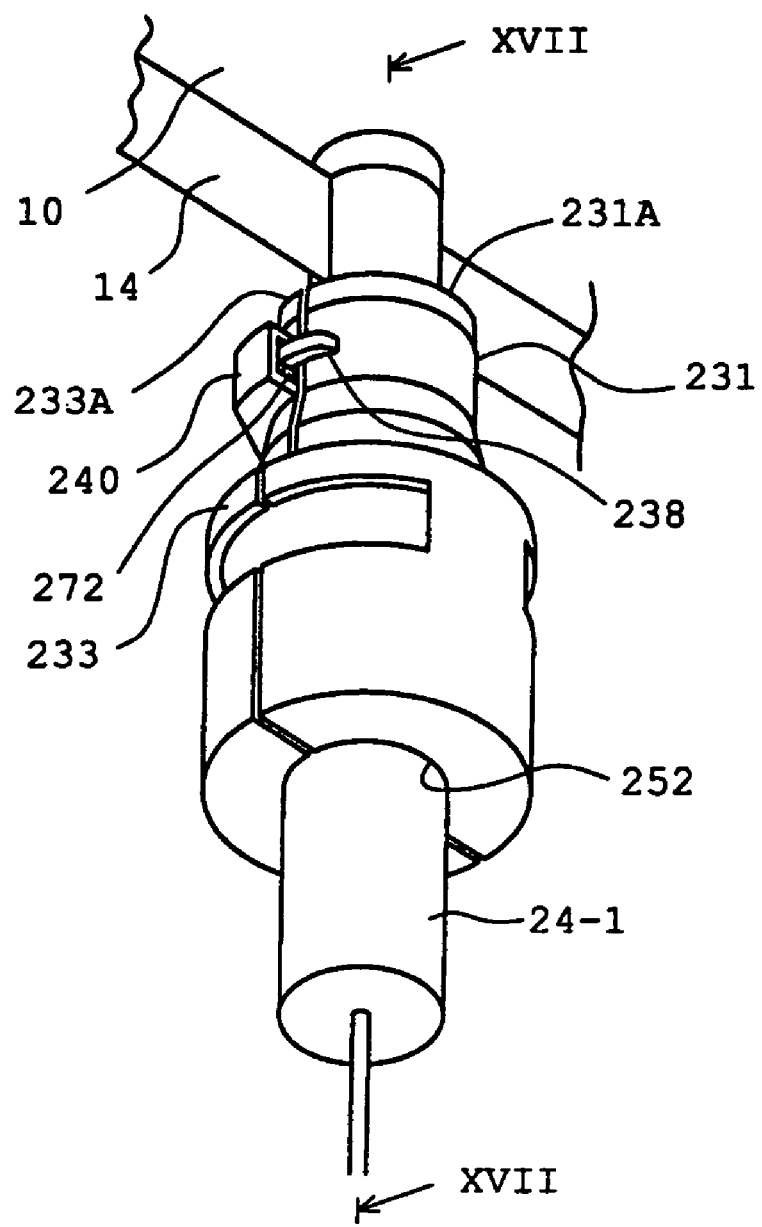
FIG. 16 is a perspective view of stopper in FIG. 15 when the split half portions are tied from the condition in FIG. 15 in a manner that a function for holding a needle is obtained.
Figure 17:
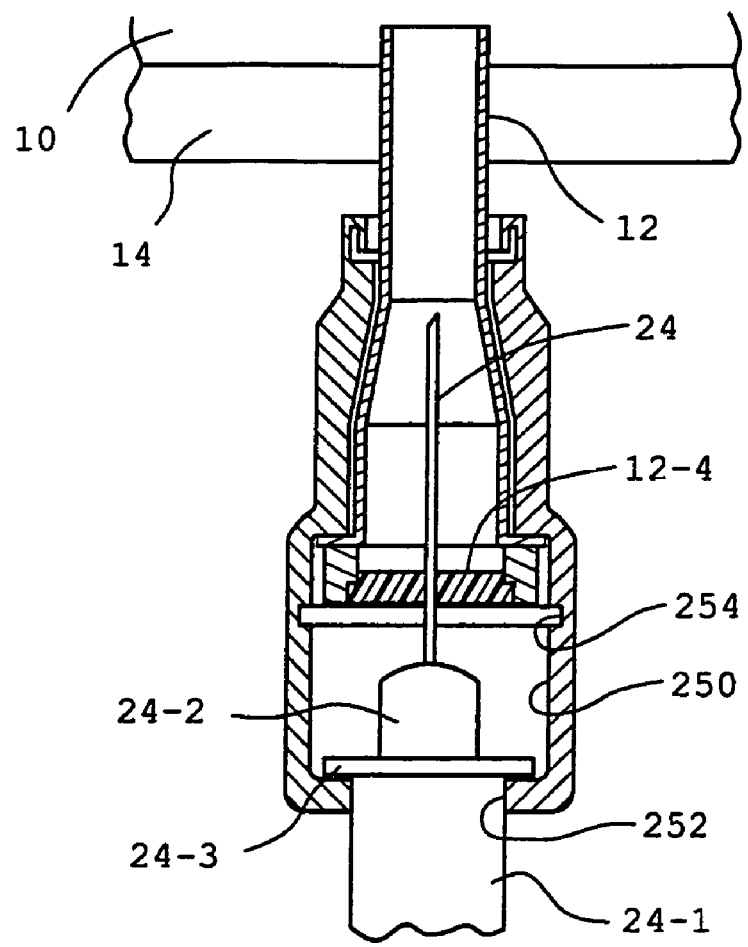
FIG. 17 is a cross-sectional view taken along lines XVII-XVII in FIG. 16.
Figure 18:
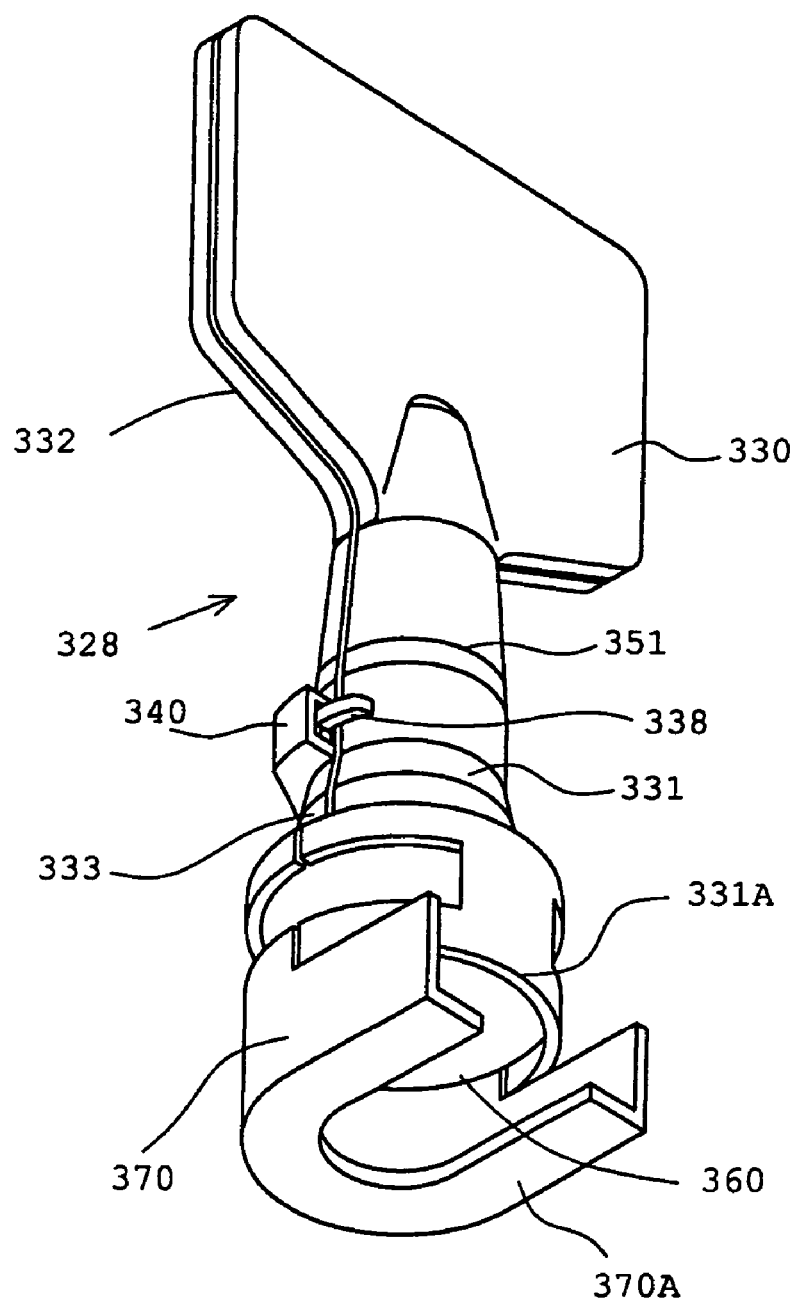
FIG. 18 illustrates a further embodiment of a stopper according to the present invention.
Figure 19:
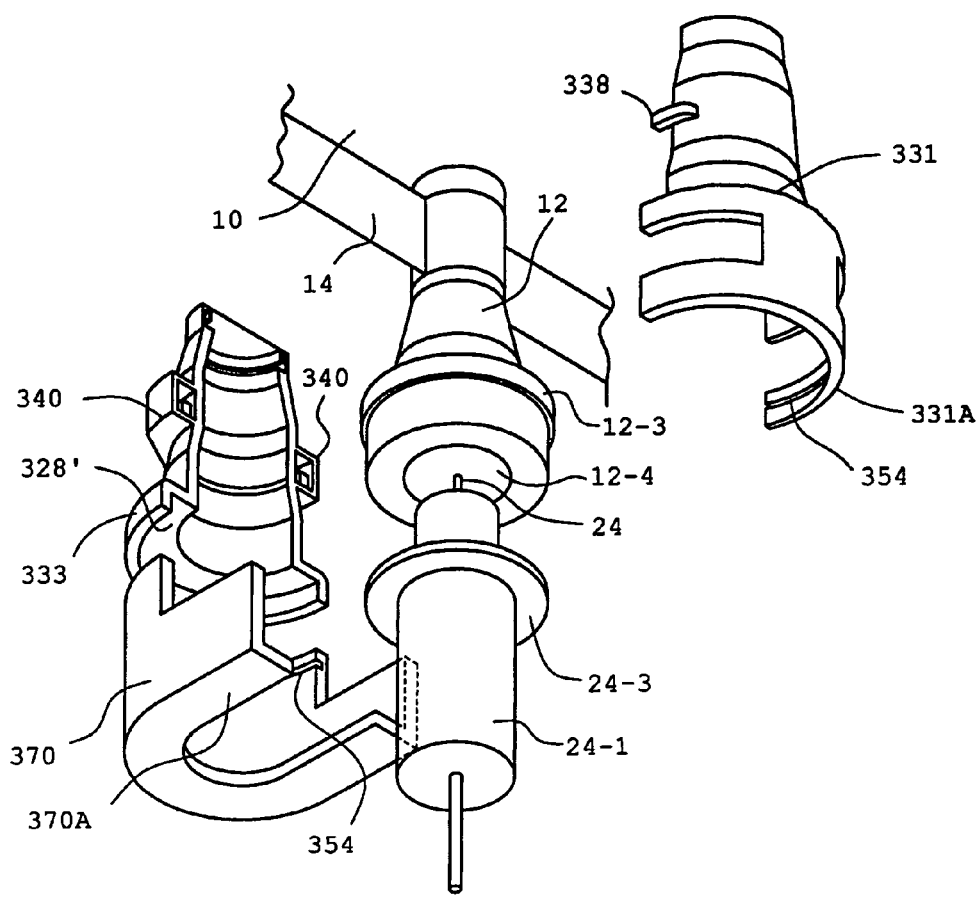
FIG. 19 is a perspective view of stopper in FIG. 18 when the stopper is used for a holder of a needle by removing flaps after the completion of opening process.
Figure 20A:
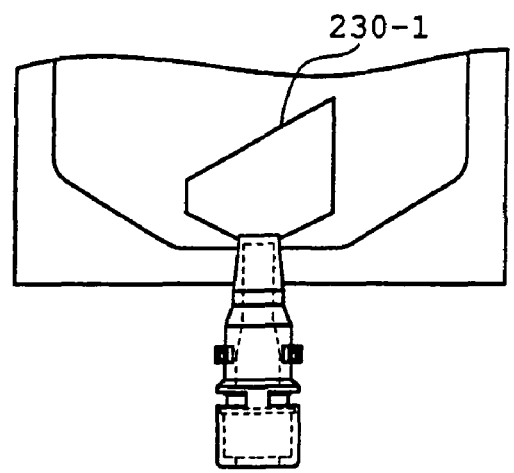
FIG. 20 illustrates modifications (a), (b) and (c) of a flap which receive hydraulic force upon the opening of the medical bag.
Figure 20B:
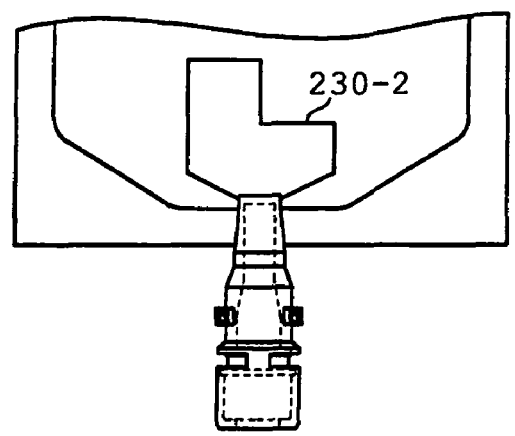
Figure 20C:
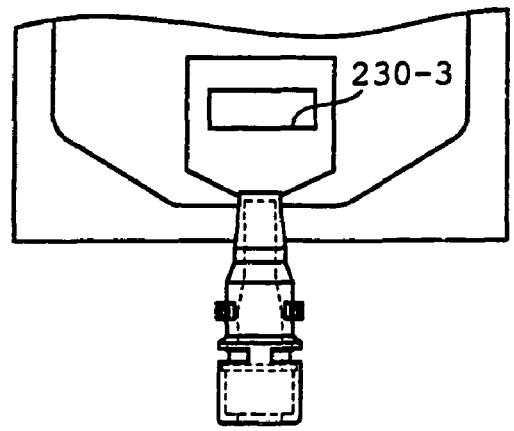

10: Medical Bag
12: Outlet Port
14: Strong Seal Portion
16: Suspension Opening
18: Weak Seal Portion
20: First Compartment
22: Second Compartment
24: Needle of Infusion Set
28, 128, 228: Medicine Discharge Stopper
30, 230: First Flap
32, 232: Second Flap
36: Integrated Hinge
38: Integrally Elongated Part
40: Engaging Groove

The invention claimed is:

1. A sealed medical storage, comprising a bag made of flexible material, a weak sealed portion for dividing a space inside the bag into a plurality of compartments, medicines being closely stored in the respective compartments, an outlet port opened to one of said compartments, and a stopper mounted on the outside of said bag wherein said stopper comprises a first flap and a second flap connected to each other via said bag, said first flap is in contact with the upper side of said bag and said second flap is in contact with the lower side of said bag, wherein said stopper arrangement prevents the medicines from being discharged from the outlet port, and wherein said stopper arrangement is such that said stopper is normally in a condition where a discharge of medicines from the bag is prevented and such that said condition is cancelled by removal of said stopper from the outlet port by a cooperation of the stopper with an expansion of the bag at a location adjacent to the outlet port as generated by an impact-like hydraulic force as generated in the bag at the instance of the breakage of said weak sealed portion, thereby allowing the medicines to be discharged from said bag.

2. The sealed medical storage according to claim 1, wherein said stopper prevents a discharge of a medicine from the bag by preventing access to the outlet port from its outer part.

3. The sealed medical storage according to claim 1, wherein said stopper prevents a discharge of a medicine from the bag by preventing a communication of a medicine in the bag to the outlet port from the outside of said bag.

4. The sealed medical storage according to claim 1, wherein said stopper further comprises a chamber outwardly opened at an end remote from said bag and a blocking member, which is detachably mounted to said chamber, said blocking member being provided for preventing any piercing by a infusion set from being occurred and wherein said contacting portion of the stopper is, at its portions contacting with the medical bag, releasable from the remaining body portion, the arrangement being such that, under a condition that said contacting portion is released from the body portion and said blocking member is removed from said chamber, the stopper is mounted to the outlet port pierced by the infusion set in a manner that the infusion set is engaged with the stopper in said chamber, thereby preventing the infusion set from being separated from the bag during the execution of an intravenous administrating operation.

5. The sealed medical storage according to claim 4, wherein said chamber is opened at the end surface of said stopper.

6. The sealed medical storage according to claim 4, wherein said chamber is opened at the side surface of said stopper.

7. The sealed medial storage according to claim 1, wherein said stopper further comprises a connecting means for connecting said first flap and said second flap.

8. The sealed medical storage according to claim 7, wherein said connecting means is of a resilient type connecting means.

9. The sealed medical storage according to claim 8, wherein said resilient connecting means is integrally formed on said stopper.

10. The sealed medical storage according to claim 7, wherein said connecting means is an interconnecting means, which is able to be broken by an outside force.

11. The sealed medical storage according to claim 7, wherein said connecting means is a hinge means for integrally connecting said first flap and second flap.

12. The sealed medial storage according to claim 1, wherein said stopper includes a chamber at an end remote from said bag.

13. The sealed medical storage according to claim 12, wherein said opening of said chamber in said stopper is formed between said first flap and said second flap.

14. The sealed medical storage according to claim 12, wherein said opening of said chamber is formed laterally in one of said first flap and said second flap.

15. A method for an infusion by a medical bag made of flexible material, and having a weak sealed portion dividing a space inside the bag into a plurality of compartments and an outlet port opened to one of said compartments, said method comprising the steps of;

providing, prior to an execution of infusion process, a stopper arranged on the bag in a manner that a medicine is prevented from being discharged from said outlet port wherein said stopper comprises a first flap and a second flap connected to each other via said bag, said first flap is in contact with the upper side of said bag and said second flap is in contact with the lower side of said bag, and wherein said stopper arrangement is such that said stopper is normally in a condition where a discharge of medicines from the bag is prevented and such that said condition is cancelled by removal of said stopper from the outlet port by a cooperation of the stopper with an expansion of the bag at a location adjacent to the outlet port as generated by an impact-like hydraulic force as generated in the bag at the instance of the breakage of said weak sealed portion, thereby allowing the medicines to be discharged from said bag;

removing said stopper from said outlet port by cooperation of the stopper with an expansion of the bag at a location adjacent to the outlet port as generated under an impact-like fluid force as generated in the bag at the instance of the breakage of said weak sealed portion; and piercing said outlet port by an infusion set so that an infusion process is commenced.

16. The method according to claim 15, wherein said step for providing the stopper comprises the step of providing the stopper having a chamber opened at its end remote from said bag and a blocking member releasably arranged in said chamber in a manner that a piercing by an infusion set is prevented, said stopper having a body part and contacting parts contacting with the medical bag and releasably connected to said body part, and wherein said method further comprises steps; of removing said contacting parts from said body part and removing the blocking member after the removal of said stopper as caused by the breakage of said weak sealed portion; and of mounting, to said outlet port, the stopper after the removal of the contacting parts as well as the blocking member, in a manner that an infusion set is housed in and engaged with the chamber of the stopper, thereby preventing the infusion set from being separated from the outlet port while an infusion process is executed.

* * * * *